(12) United States Patent
Ishii

(10) Patent No.: US 11,819,314 B2
(45) Date of Patent: Nov. 21, 2023

(54) MEDICAL APPARATUS AND TEST ASSISTING METHOD

(71) Applicant: CANON MEDICAL SYSTEMS CORPORATION, Otawara (JP)

(72) Inventor: Hideaki Ishii, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 437 days.

(21) Appl. No.: 16/988,906

(22) Filed: Aug. 10, 2020

(65) Prior Publication Data
US 2021/0059541 A1 Mar. 4, 2021

(30) Foreign Application Priority Data

Sep. 2, 2019 (JP) ................................. 2019-159589

(51) Int. Cl.
*A61B 5/02* (2006.01)
*G16H 40/60* (2018.01)
*A61B 5/00* (2006.01)
*A61B 34/10* (2016.01)
*A61F 2/24* (2006.01)
(Continued)

(52) U.S. Cl.
CPC .......... *A61B 5/02028* (2013.01); *A61B 5/021* (2013.01); *A61B 5/029* (2013.01); *A61B 5/7282* (2013.01); *A61B 34/10* (2016.02); *G16H 10/40* (2018.01); *G16H 40/60* (2018.01); *A61B 5/7267* (2013.01); *A61F 2/24* (2013.01)

(58) Field of Classification Search
CPC ..... A61B 5/02028; A61B 34/10; A61B 5/021; A61B 5/029; A61B 5/7282; A61B 5/7267; A61B 5/02; A61B 1/00045; A61B 5/7445; A61B 5/742; G16H 10/40; G16H 40/60; A61F 2/24

See application file for complete search history.

(56) References Cited

U.S. PATENT DOCUMENTS 8,086,471 B2* 12/2011 Gamboa ............ G06Q 10/1095
705/2
2004/0015233 A1* 1/2004 Jansen .................. A61F 2/2415
623/2.38
(Continued)

FOREIGN PATENT DOCUMENTS

JP 2017-217474 A 12/2017

OTHER PUBLICATIONS

Rick, "2014 AHA/ACC Guideline for the Management of Patients With Valvular Heart Disease" [DOI: 10.1161/CIR.0000000000000031 accessed on Sep. 22, 2022, Jun. 10, 2014]. (Year: 2014).*

*Primary Examiner* — Eric F Winakur
*Assistant Examiner* — Emily C Clement
(74) *Attorney, Agent, or Firm* — Oblon, McClelland, Maier & Neustadt, L.L.P.

(57) ABSTRACT

A medical apparatus according to an embodiment includes a processing circuitry. The processing circuitry is configured: to receive an input of test result information including a test result of each of tests that are related to a biological valve and were carried out at two or more different times; to estimate one of a test time for a follow-up observation of the biological valve and a test time for replacing the biological valve, on the basis of a chronological change in an open/close state of the biological valve derived from the received test result information; and to output the estimated test time.

3 Claims, 7 Drawing Sheets

(51) Int. Cl.
*G16H 10/40* (2018.01)
*A61B 5/021* (2006.01)
*A61B 5/029* (2006.01)

(56) References Cited

U.S. PATENT DOCUMENTS

| | | | |
|---|---|---|---|
| 2012/0296382 A1* | 11/2012 | Shuros | A61F 2/2403 607/7 |
| 2019/0378620 A1* | 12/2019 | Sarén | G16H 50/30 |
| 2022/0104712 A1* | 4/2022 | Sanchez Fernandez | A61B 5/0285 |

* cited by examiner

FIG.4
<LEARNING>
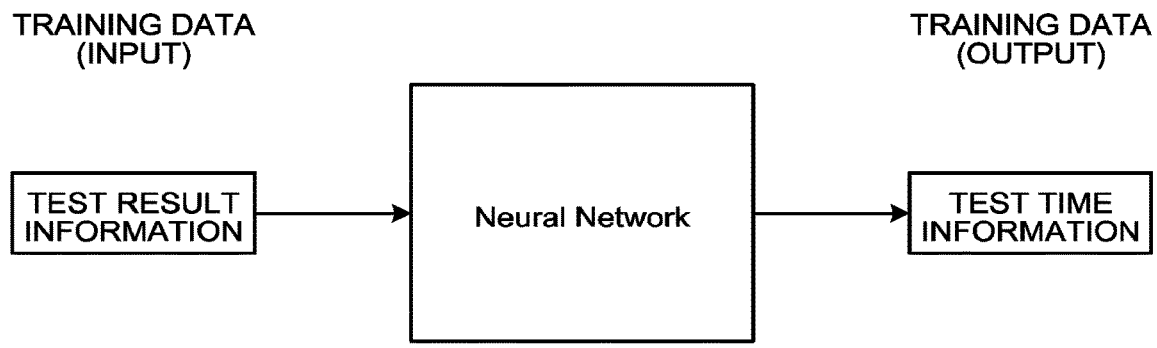
<OPERATION>

MEDICAL APPARATUS AND TEST ASSISTING METHOD

CROSS-REFERENCE TO RELATED APPLICATIONS

This application is based upon and claims the benefit of priority from Japanese Patent Application No. 2019-159589, filed on Sep. 2, 2019; the entire contents of which are incorporated herein by reference.

FIELD

Embodiments described herein relate generally to a medical apparatus and a test assisting method.

BACKGROUND

Conventionally, when blood backflows due to a defect in a heart valve such as a cardiac valvular disease, surgery is carried out to replace the valve with an artificial heart valve. Examples of artificial heart valves include mechanical valves using mechanics and biological valves using animal heart valves. When a biological valve is used, it is necessary to replace the biological valve before a dysfunction occurs. It is, however, impossible to indiscriminately identify the replacement time of biological valves, because of individual differences. It is nevertheless necessary to replace biological valves before dysfunctions occur, because dysfunctions of biological valves will be life-threatening for the patients. For this reason, medical providers such as medical doctors need to test biological valves at appropriate times.

BRIEF DESCRIPTION OF THE DRAWINGS

FIG. 4 is a drawing illustrating examples of input/output relationships of the trained model;

DETAILED DESCRIPTION

Exemplary embodiments of a medical apparatus and a test assisting method will be explained in detail below, with reference to the accompanying drawings. The medical apparatus and the test assisting method of the present disclosure are not limited to the embodiments described below.

Figure 1:
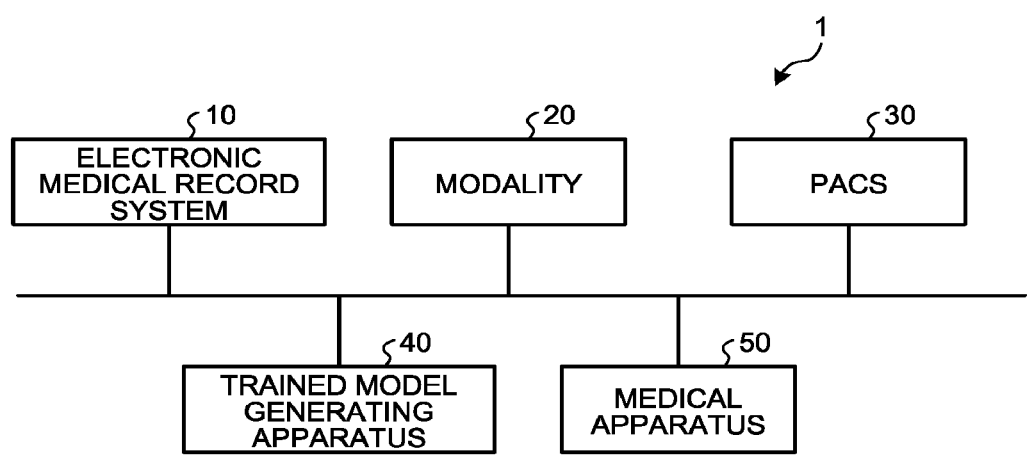
FIG. 1 is a diagram illustrating an exemplary configuration of a test assisting system according to a present embodiment.

FIG. 1 is a diagram illustrating an exemplary configuration of a test assisting system 1 according to a present embodiment. As illustrated in FIG. 1, the test assisting system 1 includes an electronic medical record system 10, a modality 20, a Picture Archiving and Communication System (PACS) 30, a trained model generating apparatus 40, and a medical apparatus 50. Further, the systems and the apparatuses are communicably connected to one another via a network. The configuration illustrated in FIG. 1 is merely an example, and the quantities of the systems and the apparatuses may arbitrarily be changed. Further, other apparatuses that are not illustrated in FIG. 1 may be connected to the network.

The electronic medical record system 10 is configured to manage electronic medical record information including patient information, diagnosis/treatment information, and the like. The patient information includes various types of information related to attributes of each patient, such as a patient identifier (ID), the patient's name, gender, height, weight, age, blood type, and the like. The diagnosis/treatment information is configured with character strings or the like arbitrarily input by medical providers such as medical doctors regarding the patient and include observations regarding injuries and/or diseases of the patient, treatment plans, and information about various types of diagnoses and treatments related to medical examinations and use of medications. The electronic medical record information may be stored in a storage or the like of the electronic medical record system 10 or may be stored in a storage or the like of another apparatuses.

The modality 20 is configured to generate a medical image by imaging an examined subject (hereinafter "patient"). The modality 20 is an image diagnosis apparatus such as an X-ray Computed Tomography (CT) apparatus, a Magnetic Resonance Imaging (MRI) apparatus, an X-ray diagnosis apparatus, or an ultrasound diagnosis apparatus. In a Radiology Information System (RIS), the modality 20 is configured to generate the medical image by imaging a site designated in imaging order information, with respect to the examined subject (e.g., a patient) designated in the imaging order information by a radiologist or the like. Further, the modality 20 is configured to transmit the generated medical image to the PACS 30.

The PACS 30 is configured to receive, store, and manage the medical image generated by the modality 20. The PACS 30 is configured to store the medical image into a storage thereof or the like, so as to be kept in correspondence with information such as a patient ID, a test ID, a test date/time, and the like. Further, the PACS 30 has stored, in a storage thereof or the like, an image interpretation report describing an interpretation result acquired by interpreting the medical image of the patient, and the like. Alternatively, the image interpretation report may be stored in a storage or the like of another apparatuses so as to be kept in correspondence with information such as the test ID.

The trained model generating apparatus 40 is configured to generate a trained model that estimates a test time of a biological valve. The trained model generating apparatus 40 is configured to acquire training data from the electronic medical record system 10, the modality 20, and the PACS 30 and to store the acquired training data into a storage thereof or the like. Alternatively, instead of the storage thereof, the trained model generating apparatus 40 may store the training data into a storage or the like of another apparatuses.

The medical apparatus 50 is configured to estimate a test time of the biological valve. Further, the medical apparatus 50 is configured to output the estimated test time in display or the like.

The electronic medical record system 10, the PACS 30, the trained model generating apparatus 40, and the medical apparatus 50 are each realized by using a computer apparatuses such as a server, a workstation, or the like.

With the configuration described above, the test assisting system 1 is configured to assist the process of identifying the test time of the biological valve, by using Artificial Intelligence (AI) such as the trained model. AI is technology for performing various types of processes such as assessing and estimating. AI is generated through machine learning such as reinforcement learning, supervised learning, unsupervised learning, deep learning, or the like. Instead of these learning methods, AI may be generated by using other methods.

Figure 2:
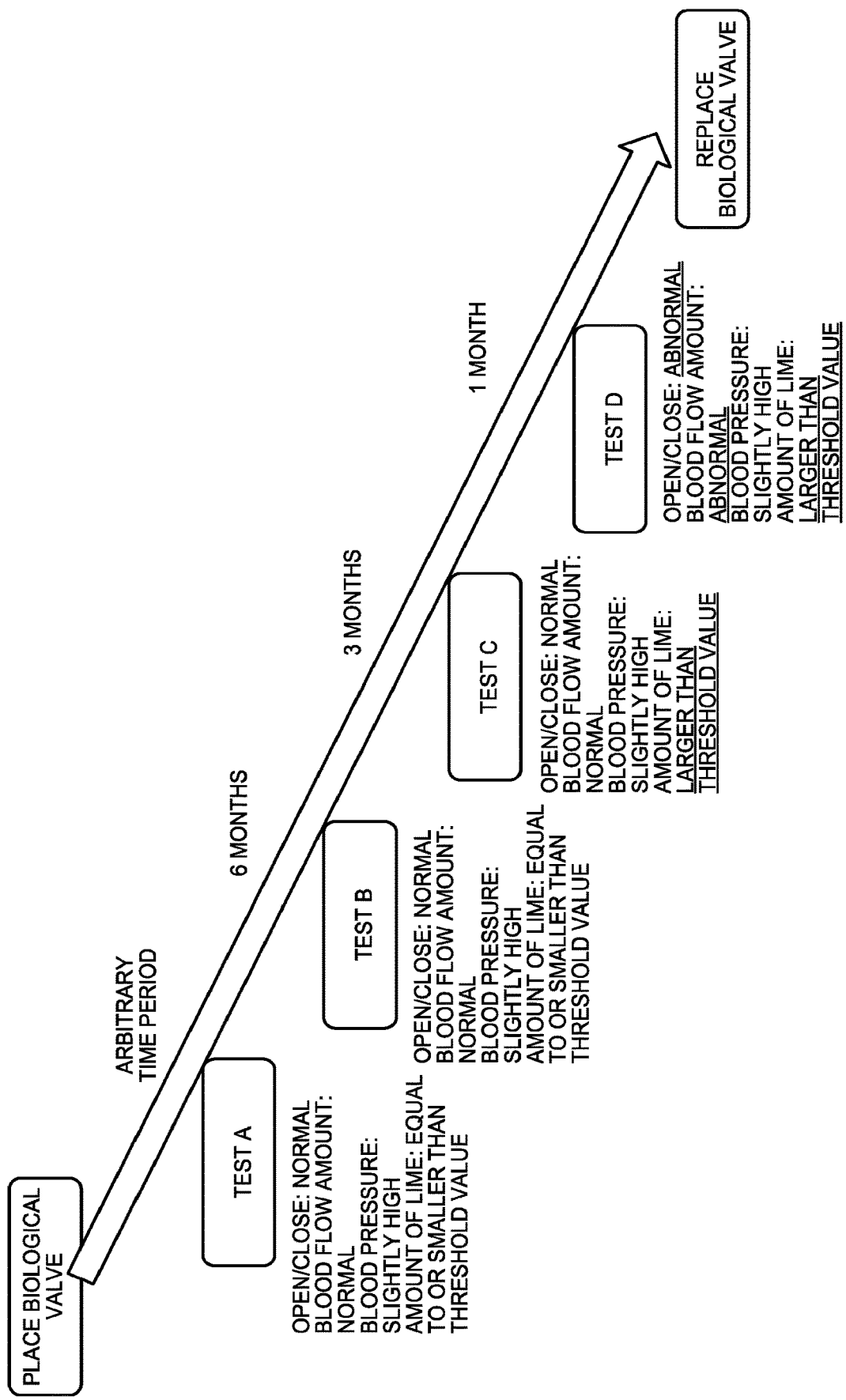
FIG. 2 is a chart for explaining an example of a trained model.

Next, the trained model will be explained. FIG. 2 is a chart for explaining an example of the trained model. In this situation, a test includes test items such as an open/close state of the biological valve, a blood flow amount of the biological valve, blood pressure, and an amount of lime adhering to the biological valve. Tests A, B, C, and D were carried out at mutually-different times.

As illustrated in FIG. 2, let us discuss an example in which test A was carried out when an arbitrary time period had elapsed since the biological valve was placed. Let us assume that the test result of test A indicates that the open/close state of the biological valve was "normal", the blood flow amount of the biological valve was "normal", the blood pressure was "slightly high", and the amount of lime was "equal to or smaller than a threshold value". The open/close state of the biological valve is determined by, for example, whether the difference between a closed state of the biological valve and an open state of the biological valve is equal to or larger than a threshold value. Alternatively, the open/close state of the biological valve may be determined by whether an open/close angle, which is the difference in the angle between when the biological valve is open and when the biological valve is closed, is equal to or larger than a threshold value. In test A, because the open/close angle of the biological valve is equal to or larger than the threshold value, the open/close state is determined to be "normal".

Let us assume that the test result of test B indicates that the open/close state of the biological valve was "normal", the blood flow amount of the biological valve was "normal", the blood pressure was "slightly high", and the amount of lime was "equal to or smaller than the threshold value". The trained model determines the test times of the next test and thereafter, on the basis of a chronological change between the test result of test A and the test result of test B. For example, on the basis of the difference corresponding to the chronological change between the open/close angle of test A and the open/close angle of test B, the trained model determines the test times of the next test and thereafter. In the example in FIG. 2, although the open/close angle of test B is within a normal range, the trained model determines that the time at which an abnormality may occur to the biological valve is approaching, on the basis of the chronological change in the open/close angle of the biological valve. In other words, the trained model determines that the next test time is in three months.

Let us assume that the test result of test C indicates that the open/close state of the biological valve was "normal", the blood flow amount of the biological valve was "normal", the blood pressure was "slightly high", and the amount of lime was "larger than the threshold value". The trained model determines the test times of the next test and thereafter, on the basis of the chronological change between the test result of test B and the test result of test C. In the example in FIG. 2, although the open/close angle of test B is within a normal range, the trained model determines that the time at which an abnormality may occur to the biological valve is further approaching, on the basis of the chronological change in the open/close angle of the biological valve. In other words, the trained model determines that the next test time is in one month.

Let us assume that the test result of test D indicates that the open/close state of the biological valve was "abnormal", the blood flow amount of the biological valve was "abnormal", the blood pressure was "slightly high", and the amount of lime was "larger than the threshold value". Further, because the test result of test D indicates the abnormalities, a medical provider such as a medical doctor determines that the biological valve needs to be replaced. With reference to FIG. 2, the trained model was described as being configured to determine the test times of the next test and thereafter on the basis of the chronological change between the two tests, namely the immediately preceding test result and the current test result. However, the number of test results used for the determination may be three or more. It is also acceptable to use all the test results since the biological valve was placed.

Next, a configuration of the trained model generating apparatus 40 according to the present embodiment will be explained.

Figure 3:
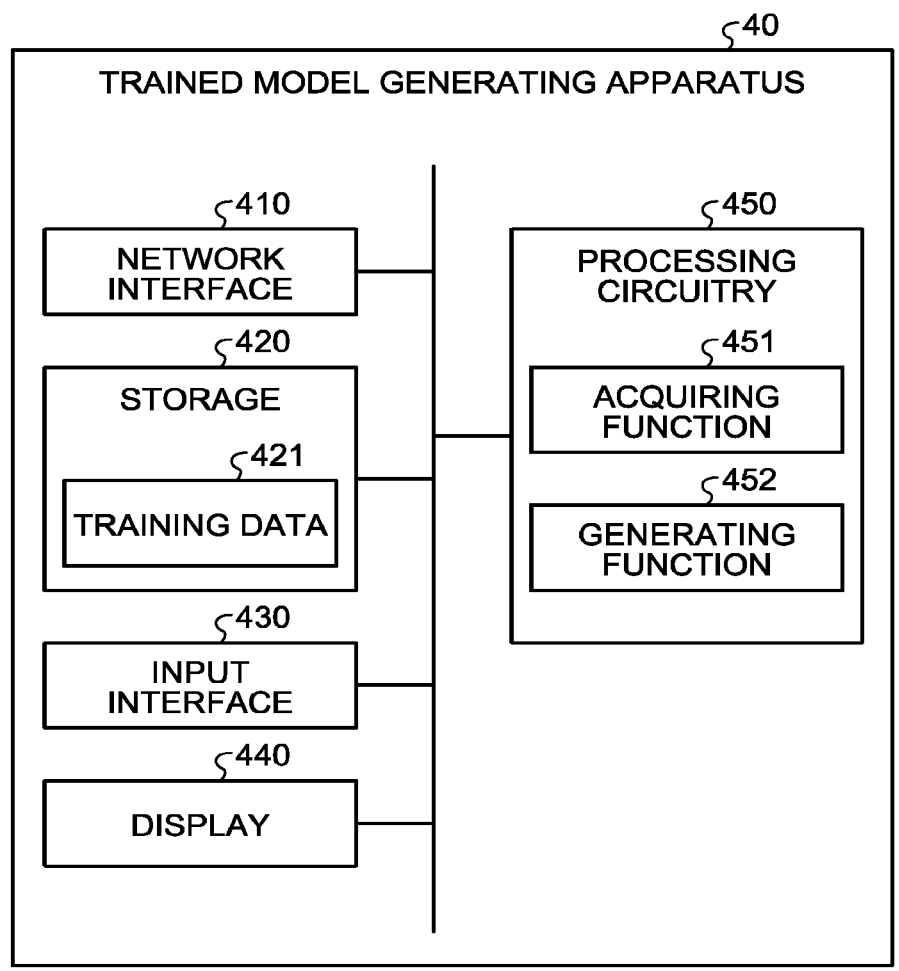
FIG. 3 is a block diagram illustrating an exemplary configuration of a trained model generating apparatus according to the present embodiment.

FIG. 3 is a block diagram illustrating an exemplary configuration of the trained model generating apparatus 40 according to the present embodiment. As illustrated in FIG. 3, the trained model generating apparatus 40 according to the present embodiment includes a network interface 410, a storage 420, an input interface 430, a display 440, and a processing circuitry 450.

The network interface 410 is connected to the processing circuitry 450 and is configured to control transfer of various types of data and communication performed with the electronic medical record system 10, the modality 20, the PACS 30, and the medical apparatus 50, via the network. More specifically, the network interface 410 is configured to receive various types of information from the systems and to output the received information to the processing circuitry 450. For example, the network interface 410 is realized by using a network card, a network adaptor, a Network Interface Controller (NIC), or the like.

The storage 420 is connected to the processing circuitry 450 and is configured to store therein various types of data. For example, the storage 420 is realized by using a semiconductor memory element such as a Random Access Memory (RAM) or a flash memory, or a hard disk, an optical disk, or the like. Further, the storage 420 has stored therein training data 421 used for generating the trained model.

The input interface 430 is configured to convert input operations received from an operator into electrical signals and to output the electrical signals to the processing circuitry 450. For example, the input interface 430 is realized by using an input device such as a trackball, a switch button, a mouse, a keyboard, a touchpad on which an input operation is performed by touching an operation surface thereof, a touch screen in which a display screen and a touchpad are integrally formed, a contactless input interface using an optical sensor, an audio input interface, and/or the like. The input interface 430 may be a controlling circuit such as a connection interface or the like configured to receive an electronic signal corresponding to an operation, from an operation device provided separately from the trained model generating apparatus 40.

The display 440 is configured to display various types of information and various types of images output from the processing circuitry 450. For example, the display 440 is realized by using a display device such as an organic Electroluminescence (EL) monitor, a liquid crystal monitor, a Cathode Ray Tube (CRT) monitor, or a touch panel. For example, the display 440 is configured to display a Graphical User Interface (GUI) for receiving instructions from the operator, various types of display-purpose image data, and various types of processing results acquired by the processing circuitry 450.

The processing circuitry 450 is configured to control constituent elements of the trained model generating apparatus 40. For example, the processing circuitry 450 is realized by using a processor. More specifically, the processing circuitry 450 according to the present embodiment includes an acquiring function 451 and a generating function 452.

The processing functions executed by the constituent elements of the processing circuitry 450 illustrated in FIG. 3, namely, the acquiring function 451 and the generating function 452, are stored in the storage 420 in the form of computer-executable programs. The processing circuitry 450 is a processor configured to realize the functions corresponding to the programs by reading and executing the programs from the storage 420. In other words, the processing circuitry 450 that has read the programs has the functions illustrated within the processing circuitry 450 in FIG. 3.

In another example, all the processing functions of the acquiring function 451 and the generating function 452 may be recorded in the storage 420 in the form of a single computer-executable program. For example, the program may be referred to as a generation processing program. In that situation, the processing circuitry 450 is configured to realize the acquiring function 451 and the generating function 452 corresponding to the generation processing program, by reading the generation processing program from the storage 420 and executing the read generation processing program.

The acquiring function 451 is configured to acquire the training data 421 used for generating the trained model. Next, input/output relationships of the trained model will be explained. FIG. 4 is a drawing illustrating examples of the input/output relationships of the trained model. In a learning, the training data 421 on the input side includes test result information. The test result information is information including a test result of each of the tests that are related to the open/close state of the biological valve and were carried out at two or more different times. In other words, the test result information includes the two or more test results of the tests related to the open/close state of the biological valve. More specifically, the test result information is information indicating open/close angles of the biological valve at the mutually-different times respectively derived from pieces of CT image data acquired at the two or more mutually-different times. Test time information is information indicating one of a test time for a follow-up observation and a test time for replacing the biological valve, the test time being determined by a medical provider such as a medical doctor on the basis of the test results. Further, the test result information includes date/time information indicating when the tests were performed.

Further, in the learning, the training data 421 on the output side includes test time information. The test time information is information indicating one of a test time for a follow-up observation of the biological valve and a test time for replacing the biological valve. For example, the test time information is information indicating the one of the test time for the follow-up observation of the biological valve and the test time for replacing the biological valve, the test time being determined by a medical provider such as a medical doctor.

The acquiring function 451 is configured to acquire the training data 421, for example, from the electronic medical record system 10, the modality 20, or the PACS 30. The acquiring function 451 is configured to store the acquired training data 421 into the storage 420.

The generating function 452 is configured to generate the trained model. More specifically, as presented under the learning in FIG. 4, the generating function 452 is configured to input the training data 421 to a neural network, for example. In other words, the generating function 452 inputs the test result information to the input side and inputs test times to the output side. The trained model generated in this manner is configured so as to output test time information indicating a test time of a biological valve of a patient, upon receiving an input of test result information.

It has been proven that the product life of biological valves varies depending on attributes of the patients such as the age of the patients and the like. For this reason, the generating function 452 is configured to generate a trained model for each of different attributes of patients. Accordingly, the trained model is able to estimate one of the test time for a follow-up observation of the biological valve and the test time for replacing the biological valve that corresponds to attributes of the patient. Alternatively, the training data 421 may include patient information related to attributes of the patient having the biological valve. In that situation, the acquiring function 451 is configured to acquire the patient information from the electronic medical record system 10. The generating function 452 is configured to generate a trained model by inputting the patient information and the test result information to the input side and inputting test times to the output side. As a result, the trained model is able to estimate one of a test time for a follow-up observation of the biological valve and a test time for replacing the biological valve that corresponds to the attributes of the patient.

Next, a configuration of the medical apparatus 50 according to the present embodiment will be explained.

Figure 5:
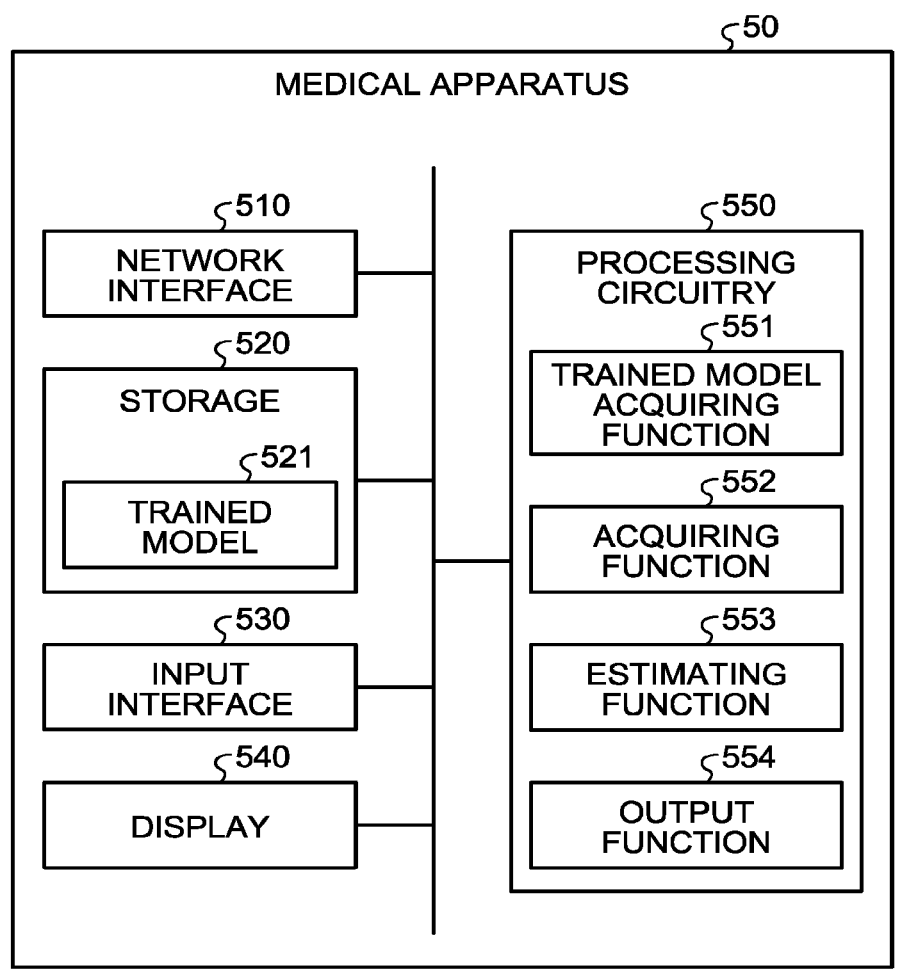
FIG. 5 is a block diagram illustrating an exemplary configuration of a medical apparatus according to the present embodiment.

FIG. 5 is a block diagram illustrating an exemplary configuration of the medical apparatus 50 according to the present embodiment. As illustrated in FIG. 5, the medical apparatus 50 according to the present embodiment includes a network interface 510, a storage 520, an input interface 530, a display 540, and a processing circuitry 550.

The network interface 510 is connected to the processing circuitry 550 and is configured to control transfer of various types of data and communication performed with the electronic medical record system 10, the modality 20, the PACS 30, and the trained model generating apparatus 40, via the network. More specifically, the network interface 510 is configured to receive various types of information from the systems and to output the received information to the processing circuitry 550. For example, the network interface 510 is realized by using a network card, a network adaptor, a Network Interface Controller (NIC), or the like.

The storage 520 is connected to the processing circuitry 550 and is configured to store therein various types of data. For example, the storage 520 is realized by using a semiconductor memory element such as a Random Access Memory (RAM) or a flash memory, or a hard disk, an optical disk, or the like. Further, the storage 520 has stored therein a trained model 521 configured to estimate test times of biological valves.

The input interface 530 is configured to convert input operations received from an operator into electrical signals and to output the electrical signals to the processing circuitry 550. For example, the input interface 530 is realized by using an input device such as a trackball, a switch button, a mouse, a keyboard, a touchpad on which an input operation is performed by touching an operation surface thereof, a touch screen in which a display screen and a touchpad are integrally formed, a contactless input interface using an optical sensor, an audio input interface, and/or the like. The input interface 530 may be a controlling circuit such as a connection interface or the like configured to receive an electronic signal corresponding to an operation, from an operation device provided separately from the medical apparatus 50.

The display 540 is configured to display various types of information and various types of images output from the processing circuitry 550. For example, the display 540 is realized by using a display device such as an organic Electroluminescence (EL) monitor, a liquid crystal monitor, a Cathode Ray Tube (CRT) monitor, or a touch panel. For example, the display 540 is configured to display a Graphical User Interface (GUI) for receiving instructions from the operator, various types of display-purpose image data, and various types of processing results acquired by the processing circuitry 550.

The processing circuitry 550 is configured to control constituent elements of the medical apparatus 50. For example, the processing circuitry 550 is realized by using a processor. More specifically, the processing circuitry 550 according to the present embodiment includes a trained model acquiring function 551, an acquiring function 552, an estimating function 553, and an output function 554.

The processing functions executed by the constituent elements of the processing circuitry 550 illustrated in FIG. 5, namely, the trained model acquiring function 551, the acquiring function 552, the estimating function 553, and the output function 554, are stored in the storage 520 in the form of computer-executable programs. The processing circuitry 550 is a processor configured to realize the functions corresponding to the programs by reading and executing the programs from the storage 520. In other words, the processing circuitry 550 that has read the programs has the functions illustrated within the processing circuitry 550 in FIG. 5.

In another example, all the processing functions of the trained model acquiring function 551, the acquiring function 552, the estimating function 553, and the output function 554 may be recorded in the storage 520 in the form of a single computer-executable program. For example, the program may be referred to as a display processing program. In that situation, the processing circuitry 550 is configured to realize the trained model acquiring function 551, the acquiring function 552, the estimating function 553, and the output function 554 corresponding to the display processing program, by reading the display processing program from the storage 520 and executing the read display processing program.

The trained model acquiring function 551 is configured to acquire the trained model 521 from the trained model generating apparatus 40. Further, the trained model acquiring function 551 is configured to store the acquired trained model 521 into the storage 520.

The acquiring function 552 is an example of a receiving unit. The acquiring function 552 is configured to receive an input of the test result information including the test result of each of the tests that are related to the biological valve and were carried out at two or more different times. For example, the acquiring function 552 is configured to acquire the test result information from the electronic medical record system 10, the modality 20, or the PACS 30. The test result information includes information indicating the open/close state of the biological valve such as the open/close angle of the biological valve. Further, when estimating a test time corresponding to attributes of the patient, the acquiring function 552 is configured to receive inputs of the patient information related to the attributes of the patient having the biological valve and the test result information. For example, the acquiring function 552 is configured to acquire the patient information from the electronic medical record system 10.

The estimating function 553 is an example of an estimating unit. On the basis of a chronological change in the open/close state of the biological valve derived from the test result information received by the acquiring function 552, the estimating function 553 is configured to estimate one of a test time for a follow-up observation of the biological valve and a test time for replacing the biological valve. More specifically, the estimating function 553 is configured to estimate the test time of the biological valve, by inputting the test result information to the trained model 521 that estimates the test time of the biological valve on the basis of the test result information. In other words, the estimating function 553 is configured to estimate the test time of the biological valve, by inputting the test result information to the trained model 521 acquired by the trained model acquiring function 551 from the trained model generating apparatus 40.

Further, when estimating a test time corresponding to attributes of the patient, the estimating function 553 is configured to estimate one of a test time for a follow-up observation of the biological valve and a test time for replacing the biological valve, on the basis of the patient information and the test result information. Further, when estimating a test time corresponding to the attributes of the patient by using the trained model 521, the estimating function 553 is configured to use the patient information in accordance with the trained model 521 acquired by the trained model acquiring function 551. When having acquired the trained model 521 generated for each of the attributes of patients, the estimating function 553 is configured to select one of the trained models 521 according to the attributes of the patient indicated by the patient information acquired by the acquiring function 552. Further, the estimating function 553 is configured to estimate a test time of the biological valve, by inputting the test result information to the trained model 521 that estimates the test time of the biological valve on the basis of the test result information. In contrast, when having acquired a trained model 521 generated by inputting attribute information, the estimating function 553 is configured to estimate a test time of the biological valve, by inputting the attribute information and the test result information to the trained model 521 that estimates the test time of the biological valve on the basis of the attribute information and the test result information.

Figure 6:
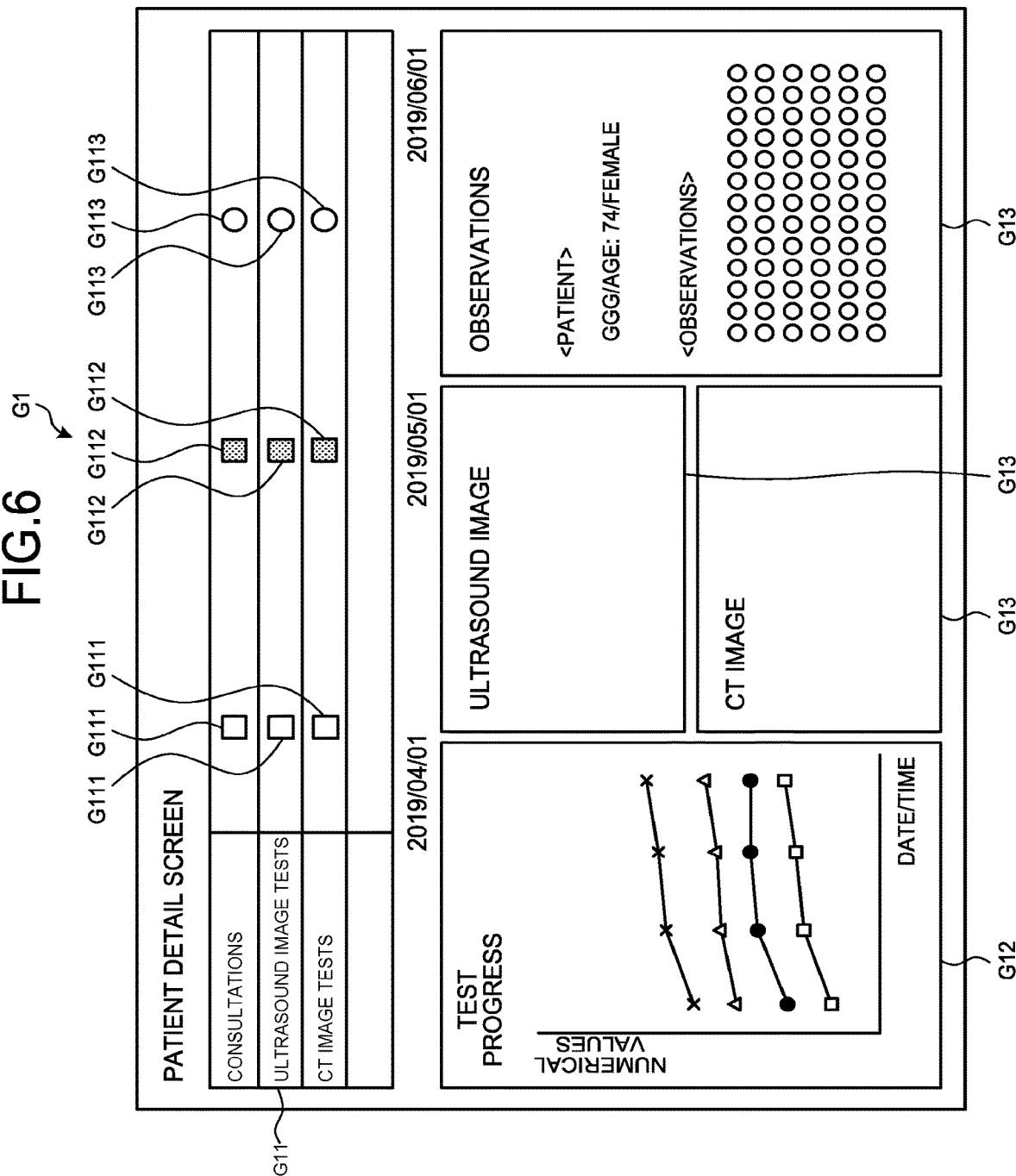
FIG. 6 is a drawing illustrating an example of a test schedule screen.

The output function 554 is an example of an output unit. The output function 554 is configured to output the test time estimated by the estimating function 553. For example, the output function 554 is configured to cause a test schedule screen G1 to display the test time estimated by the estimating function 553. FIG. 6 is a drawing illustrating an example of the test schedule screen G1. The test schedule screen G1 is a screen displaying a test schedule of a selected patient. The test schedule screen G1 includes a time-series display region G11, a test progress display region G12, a detail display region G13.

The time-series display region G11 is a region for displaying events arranged in a time series for each type of events. The time-series display region G11 in FIG. 6 displays consultations, ultrasound image tests, and CT image tests, as types of events. Possible examples of the types of events are not limited to consultations, ultrasound image tests, and CT image tests and may include other events.

The time-series display region G11 contains non-display icons G111, current-display icons G112, and schedule icons G113. The non-display icons G111 and the current-display icons G112 are icons indicating test times at which tests were carried out on the biological valve. Further, the non-display icons G111 are icons indicating events that are among the events of the patient, but are not displayed in the detail display region G13. The current-display icons G112 are icons indicating events that are among the events of the patient and are displayed in the detail display region G13. Further, the schedule icons G113 are icons indicating the test dates/times of the biological valve estimated by the estimating function 553. Furthermore, the schedule icons G113 may receive an operation to make an appointment for a test of an event corresponding to any of the test dates/times estimated by the estimating function 553.

As described above, the output function 554 is configured to output the test schedule screen G1 that has arranged thereon, in the time series, the non-display icons G111 and the current-display icons G112 serving as examples of the first icon indicating the test times at which tests were carried out on the biological valve, as well as the schedule icons G113 serving as examples of the second icon indicating the test times of the biological valve estimated by the estimating function 553.

The test progress display region G12 is a display region for displaying a graph acquired by plotting test results of the biological valve. Further, the test progress display region G12 may have predicted values plotted, which may be exhibited when the tests are carried out at the test times indicated by the schedule icons G113.

The detail display region G13 is a region for displaying details of the icons selected in the time-series display region G11. The test schedule screen G1 in FIG. 6 includes a detail display region G13 displaying observations corresponding to the current-display icon G112 for the "consultations", another detail display region G13 displaying an ultrasound image corresponding to the current-display icon G112 for the "ultrasound image tests", and yet another detail display region G13 displaying a CT image corresponding to the current-display icon G112 for the "CT image tests". In other words, the output function 554 is configured to output the test schedule screen G1 including the non-display icons G111, the current-display icons G112, and the schedule icons G113 that are arranged in the time series, as well as the test results of the biological valve tested at the test times indicated by the current-display icons G112.

Figure 7:
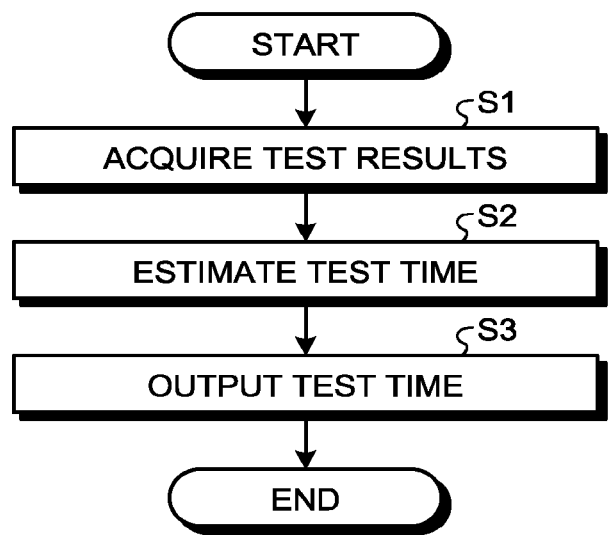
FIG. 7 is a flowchart illustrating a processing procedure of an estimating process performed by the medical apparatus according to the present embodiment.

Next, an estimating process performed by the medical apparatus 50 according to the present embodiment will be explained. FIG. 7 is a flowchart illustrating a processing procedure of the estimating process performed by the medical apparatus 50 according to the present embodiment.

The acquiring function 552 acquires test result information including the test result of each of the tests that are related to the biological valve and were carried out at two or more different times (step S1).

On the basis of a chronological change in the open/close state of the biological valve derived from the test result information, the estimating function 553 estimates a test time of the biological valve (step S2). For example, the estimating function 553 estimates one of a test time for a follow-up observation of the biological valve and a test time for replacing the biological valve.

The output function 554 outputs the estimated test time (step S3). For example, the output function 554 causes the test schedule screen G1 to display the test time.

The medical apparatus 50 thus ends the estimating process.

As explained above, in the medical apparatus 50 according to the present embodiment, the acquiring function 552 is configured to receive the input of the test result information including the test result of each of the tests that are related to the biological valve and were carried out at the two or more different times. On the basis of the chronological change in the open/close state of the biological valve derived from the test result information received by the acquiring function 552, the estimating function 553 is configured to estimate one of the test time for the follow-up observation of the biological valve and the test time for replacing the biological valve. Further, the output function 554 is configured to output the test time estimated by the estimating function 553. For example, the output function 554 causes the time-series display region G11 on the test schedule screen G1 to display the test time estimated by the estimating function 553. Accordingly, medical providers such as medical doctors are able to reference the test time of the biological valve displayed on the test schedule screen G1. Consequently, the medical apparatus 50 is able to assist the process of identifying the test time of the biological valve.

In the above embodiment, the example was explained in which the estimating function 553 is configured to estimate the test time of the biological valve, on the basis of the chronological change in the open/close state of the biological valve derived from the test result information.

In this situation, when there is an abnormality in the open/close state of the biological valve, the blood flow amount and the blood pressure also exhibit abnormal values because blood does not flow in a normal manner. For this reason, it is possible to estimate the open/close state of the biological valve on the basis of the blood flow amount of the biological valve and the blood pressure. Accordingly, the test result information may include information indicating test results of the blood flow amount of the biological valve and the blood pressure. In that situation, the acquiring function 451 is configured to acquire the test result information including the blood flow amount of the biological valve and the blood pressure measured from an ultrasound image or the like. Further, the generating function 452 is configured to generate a trained model 521, by inputting the test result information including the blood flow amount of the biological valve and the blood pressure and the test time information to a neural network or the like. The acquiring function 552 is configured to receive an input of the test result information including the blood flow amount of the biological valve and the blood pressure. On the basis of a chronological change in the open/close state of the biological valve derived from the blood flow amount of the biological valve and the blood pressure included in the test result information, the estimating function 553 is configured to estimate a test time of the biological valve. For example, the estimating function 553 is configured to estimate the test time of the biological valve, by inputting the test result information indicating the blood flow amount of the biological valve and the blood pressure, to the trained model 521 generated by the generating function 452.

In the above embodiment, the example was explained in which the estimating function 553 is configured to estimate the test time of the biological valve, on the basis of the open/close state of the biological valve derived from the test result information. In this regard, when lime is adhering to the biological valve, the opening and closing of the biological valve is inhibited by the lime. For this reason, it is possible to estimate an open/close state of the biological valve on the basis of the amount of lime adhering to the biological valve. Accordingly, the test result information may include information indicating a test result of the amount of lime adhering to the biological valve. In this situation, the acquiring function 451 is configured to acquire the test result information including the amount of lime adhering to the biological valve that was measured from CT image data, which is three-dimensional data. Further, the generating function 452 is configured to generate a trained model 521 by inputting the test result information indicating the amount of lime adhering to the biological valve and the test time information to a neural network or the like. The acquiring function 552 is configured to receive an input of the test result information including the amount of lime adhering to the biological valve. On the basis of a chronological change in the open/close state of the biological valve derived from the amount of lime adhering to the biological valve that is included in the test result information, the estimating function 553 is configured to estimate a test time of the biological valve. For example, the estimating function 553 is configured to estimate the test time of the biological valve, by inputting the test result information indicating the amount of lime adhering to the biological valve, to the trained model 521 generated by the generating function 452.

In the above embodiment, the example was explained in which the estimating function 553 is configured to estimate the test time by using the trained model 521. However, the estimating function 553 may estimate the test time by using other methods besides the trained model 521. For example, the estimating function 553 may estimate the test time by using an information table indicating test times corresponding to chronological changes in the open/close state of the biological valve derived from the test result information. Further, when there is an information table for each of various attributes of patients, the estimating function 553 may estimate a test time on the basis of the patient information and the test result information.

Further, in the above embodiment, the example was explained in which the processing functions are realized by the single processing circuitries (the processing circuitries 450 and 550); however, possible embodiments are not limited to this example. For instance, each of the processing circuitries 450 and 550 may be configured by combining together a plurality of independent processors, so that the processing functions are realized as a result of the processors executing the programs. Further, the processing functions of each of the processing circuitries 450 and 550 may be realized as being distributed among or integrated together into one or more processing circuitries 450, 550, as appropriate.

The term "processor" used above in the explanations of the above embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). Further, instead of saving the programs in a memory, it is also acceptable to directly incorporate the programs into the circuits of the processors. In that situation, the processors realize the functions by reading and executing the programs incorporated in the circuits thereof. Further, each of the processors of the present embodiments does not necessarily have to be structured as a single circuit. It is also acceptable to structure one processor by combining together a plurality of independent circuits so as to realize the functions thereof.

In the present example, the programs executed by the processors are provided as being incorporated, in advance, in a Read Only Memory (ROM), a storage unit, or the like. The programs may be provided as being recorded on a computer-readable storage medium such as a Compact Disk Read-Only Memory (CD-ROM), a Flexible Disk (FD), a Compact Disk Recordable (CD-R), a Digital Versatile Disk (DVD), or the like, in a file in a format that is installable or executable by these devices. Further, the programs may be stored in a computer connected to a network such as the Internet so as to be provided or distributed as being downloaded via the network. For example, the programs are structured with modules including the functional units. In the actual hardware, as a result of a CPU reading and executing the programs from a storage medium such as a ROM, the modules are loaded into a main memory and generated in the main memory.

The constituent elements of the apparatuses in the drawings are based on functional concepts. Thus, it is not necessary to physically configure the constituent elements as indicated in the drawings. In other words, specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a program analyzed and executed by the CPU or may be realized as hardware using wired logic.

Further, it is possible to realize the medical information display method explained in the above embodiment, by causing a computer such as a personal computer or a workstation to execute a program prepared in advance. The program may be distributed via a network such as the Internet. Further, the program may be executed, as being recorded on a computer-readable recording medium such as a hard disk, a flexible disk (FD), a CD-ROM, a Magneto-Optical (MO) disk, a DVD, or the like and being read from the recording medium by a computer.

According to at least one aspect of the embodiments described above, it is possible to assist the process of identifying the test times of the biological valve.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical apparatus, comprising:
    processing circuitry configured to
        receive an input of test result information and patient information, the test result information including an open/close angle of a biological valve at each of two or more different times, the patient information representing an attribute of a patient having the biological valve, select a trained model according to the patient information, from a plurality of trained models for respective attributes of the patient;

estimate a test time for replacing the biological valve by inputting the test result information into the selected trained model; and display, on a display, an image including a first display region in which a first icon and a second icon are arranged in a time series, the first icon indicating the test time at which the biological valve was tested, the second icon indicating the estimated test time of the biological valve, and a second display region displaying a graph acquired by plotting the test result information.

2. The medical apparatus according to claim 1, wherein the processing circuitry is further configured to receive an operation to make an appointment for a test at the estimated test time.

3. A test assisting method, comprising:

receiving an input of test result information and patient information, the test result information including an open/close angle of a biological valve at each of two or more different times, the patient information representing an attribute of a patient having the biological valve;

selecting a trained model according to the patient information, from a plurality of trained models for respective attributes of the patient;

estimating a test time for replacing the biological valve by inputting the test result information to the selected trained model; and displaying, on a display, an image including a first display region in which a first icon and a second icon are arranged in a time series, the first icon indicating the test time at which the biological valve was tested, the second icon indicating the estimated test time of the biological valve, and a second display region for displaying a graph acquired by plotting the test result information.

* * * * *